United States Patent [19]

Kihara et al.

[11] Patent Number: 4,973,588

[45] Date of Patent: Nov. 27, 1990

[54] IMIDAZOLE DERIVATIVES HAVING ANTI-HYPOXIA PROPERTIES

[75] Inventors: Noriaki Kihara; Ikuo Tomino; Mitsuyuki Takesue, all of Waki; Takafumi Ishihara, Toyonaka, all of Japan

[73] Assignee: Mitsui Petrochemical Industries, Ltd., Tokyo, Japan

[21] Appl. No.: 308,523

[22] Filed: Feb. 10, 1989

[30] Foreign Application Priority Data

Feb. 10, 1988 [JP] Japan ................................. 63-27770

[51] Int. Cl.$^5$ .................. A61K 31/535; C07D 273/01
[52] U.S. Cl. .................... 514/235.8; 514/304; 514/318; 514/326; 544/139; 544/131; 546/125; 546/193; 546/210; 546/278

[58] Field of Search ............... 548/341, 336; 544/58.4, 544/139, 370, 131, 364, 122; 546/193, 210, 278, 125; 514/397, 399, 227.8, 235.8, 252, 326, 318, 341, 304

[56] References Cited

U.S. PATENT DOCUMENTS

| | | | |
|---|---|---|---|
| 4,048,188 | 9/1977 | Baker | 548/341 |
| 4,678,798 | 7/1987 | Rentzea | 514/383 |

*Primary Examiner*—Mary C. Lee
*Assistant Examiner*—Jacqueline Haley
*Attorney, Agent, or Firm*—Sherman and Shalloway

[57] ABSTRACT

A novel N-substituted imidazole or thioimidazole derivative and a pharmacologically acceptable acid addition salt thereof, which have a brain function-improving action, are disclosed. The derivative or salt is used as an effective ingredient of a brain function-improving medicine.

22 Claims, No Drawings

IMIDAZOLE DERIVATIVES HAVING ANTI-HYPOXIA PROPERTIES

BACKGROUND OF THE INVENTION

(1) Field of the Invention

The present invention relates to a novel imidazole derivative, a salt thereof and a medicine comprising the derivative or salt as an active ingredient. More particularly, the present invention relates to a novel N-substituted imidazole derivative or thioimidazole derivative valuable as an anti-hypoxia action and anti-brain-ischemia medicine, a pharmacologically acceptable acid addition salt thereof and an anti-hypoxia action and anti-brain-ischemia medicine comprising the imidazole derivative or acid addition salt or a mixture thereof as an effective ingredient.

(2) Description of the Related Art

For example, the specifications of West German Patent No. 2,805,166, West German Patent No. 2,823,197 and U.S. Pat. No. 4,218,458 disclose certain thioimidazole derivatives, and it is known that these compounds have pharmacological actions such as an antibacterial activity.

Furthermore, certain imidazole derivatives are disclosed in Japanese Patent Application Laid-Open Specifications Nos. 32463/81, 128767/81, 128768/81, 149273/82, 18365/83 and 105970/83, and it is known that these compounds have pharmacological actions such as an antihypertensive action a diuretic action, an anti-thrombic action, an analgesic action, a sedative action, an anti-inflammatory action and a tranquilizing action.

SUMMARY OF THE INVENTION

The N-substituted imidazole derivative and thioimidazole derivative of the present invention are novel compounds having substituents quite different from those of the above-mentioned known imidazole derivatives, and they have an excellent anti-hypoxia and anti-brain-ischemia action not possessed by these known imidazole derivatives.

In accordance with one aspect of the present invention, there is provided an N-substituted imidazole derivative represented by following general formula [I] or a pharmacologically acceptable acid addition salt thereof:

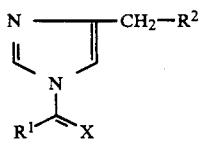

wherein $R^1$ stands for $NR^3R^4$ or $OR^5$, (in which $R^3$ and $R^4$ independently stand for a lower alkyl group, a lower alkenyl group, a cycloalkyl group or a lower alkoxyl group, or $R^3$ and $R^4$ form a 5- to 8-membered ring together with the nitrogen atom to which $R^3$ and $R^4$ are bonded, with the proviso that said ring may contain a nitrogen atom, a sulfur atom or an oxygen atom therein, said ring may contain a lower alkyl group or a lower alkoxyl group as a ring substituent and two alkyl substituents, on said ring may further form a ring, and $R^5$ stands for a lower alkyl group), $R^2$ stands for a phenyl group, a phenoxy group or a pyridyl group, which may be substituted by a lower alkyl group, a lower alkoxyl group, a halogen atom or an amino group, and X stands for an oxygen atom or a sulfur atom.

In accordance with another aspect of the present invention, there is provided a thioimidazole derivative represented by the following general formula [II] or a pharmacologically acceptable acid addition salt thereof:

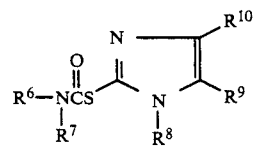

wherein $R^6$ and $R^7$ independently stand for a lower alkyl group or $R^6$ and $R^7$ form a 5- to 7-membered ring together with the nitrogen atom to which $R^6$ and $R^7$ are bonded, with the proviso that said ring may contain a nitrogen atom, a sulfur atom or an oxygen atom therein, said ring may have a lower alkyl group or a lower alkoxy group as a ring substituent and when substituents are present on adjacent carbon atoms of said ring, the substituents may form a benzene ring together with the carbon atoms to which they are bonded, $R^8$ stands for an hydrogen atom, a lower alkyl group, a cycloalkyl group, a phenyl group, a loweralkylcarbonyl group, a lower alkoxycarbonyl group, a lower dialkylaminocarbonyl group, a cyclic aminocarbonyl group or a pyridyl group which may be substituted by a halogen atom or a nitro group, $R^7$ and $R^8$ may be one carbonyl group forming a ring, $R^9$ stands for a hydrogen atom, a lower alkyl group or a lower alkoxycarbonyl group, and $R^{10}$ stands for a lower alkyl group, a lower alkoxyl group, a phenyl group which may be substituted by a halogen atom, or a hydrogen atom.

In accordance with still another aspect of the present invention, there is provided a medicine having an anti-hypoxia or anti-brain-ischemia action, which comprises at least one member selected from said imidazole derivatives and pharmacologically acceptable acid addition salts thereof as an effective ingredient.

In the N-substituted imidazole derivative represented by the above-mentioned formula [I], as the alkyl group as the substituent of $R^2$ or as $R^3$, $R^4$ and $R^5$, there can be mentioned, for example, a methyl group, an ethyl group, a propyl group, an isopropyl group, a butyl group and a t-butyl group. As the cycloalkyl group as $R^3$ and $R^4$, there can be mentioned, for example, a cyclopentyl group, a cyclohexyl group and a cycloheptyl group. As the halogen atom as the substituent of $R^2$, there can be mentioned, for example, a chlorine atom, a bromine atom and a fluorine atom. As the lower alkoxyl group as the substituent of $R^2$ or as $R^3$ and $R^4$, there can be mentioned, for example, a methoxyl group, an ethoxyl group, a propoxyl group, an isopropoxyl group and a butoxyl group. As the lower alkenyl group as $R^3$ and $R^4$, there can be mentioned, for example, an allyl group and a propenyl group.

In the thioimidazole derivative represented by the above-mentioned formula [II], as the lower alkyl group as $R^6$, $R^7$, $R^8$, $R^9$ and $R^{10}$, there can be mentioned, for example, a methyl group, an ethyl group, a propyl group, an isopropyl group, a butyl group, an isobutyl group and a t-butyl group. As the cycloalkyl group as $R^8$, there can be mentioned, for example, a cyclopentyl group, a cyclohexyl group and a cycloheptyl group. As the halogen atom as the substituent or $R^8$ and $R^{10}$, there can be mentioned, for example, a chlorine atom, a bromine atom and a fluorine atom. As the lower alkoxyl group as $R^6$, $R^7$ and $R^{10}$, there can be mentioned, for example, a methoxyl group, an ethoxyl group, a propoxyl group, an isopropoxyl group and a butoxyl group. As the lower alkylcarbonyl group as $R^8$, there can be mentioned, an acetyl group, a propionyl group, an isopropionyl group and a butyloyl group. As the lower alkoxycarbonyl group as $R^8$, there can be mentioned, for example, a methoxycarbonyl group, an ethoxycarbonyl group, a propoxycarbonyl group, an isopropoxycarbonyl group and a butoxycarbonyl group. As the lower dialkylaminocarbonyl group as $R^8$, there can be mentioned, for example, a dimethylaminocarbonyl group, a diethylaminocarbonyl group, a dipropylaminocarbonyl group, diisopropylaminocarbonyl group and a dibutylaminocarbonyl group. As the cyclic aminocarbonyl group as $R^8$, there can be mentioned, for example, a pyrrolidinocarbonyl group and a piperidinocarbonyl group.

The compound of the present invention may be either in the free state or in the form of a salt, for example, an acid addition salt. As the acid addition salt, there can be mentioned pharmacologically acceptable salts such as a hydrochloride, a hydrobromide, a sulfuric acid salt, a nitric acid salt, a sulfonic acid salt, a formic acid salt, a tartaric acid salt, a maleic acid salt, a citric acid salt, a benzoic acid salt, a salicylic acid salt and an ascorbic acid salt.

The N-substituted imidazole and thioimidazole derivatives of the present invention and the acid addition salts thereof show, singly or in the form of a mixture thereof, excellent antibrain-ischemia action and antihypobaric-hypoxia action, and therefore, they are valuable as a brain function-improving agent.

The compound of the present invention can be administered as it is, or the compound can be prepared into various medicine forms and can be administered orally or non-orally.

DETAILED DESCRIPTION OF THE PREFERRED EMBODIMENTS

The synthesis of the imidazole derivative of the present invention will now be described.

1. Synthesis of N-Substituted Imidazole Derivative

The N-substituted imidazole derivative represented by the above-mentioned formula [I] is synthesized according to the process represented by the following reaction formula:

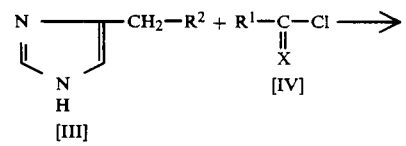

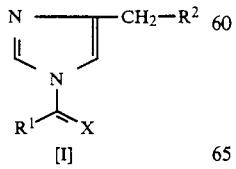

More specifically, the compound [I] can be prepared by reacting compounds [III] and [IV] in the presence of an inorganic base such as calcium carbonate, sodium carbonate, sodium hydroxide or potassium hydroxide or an organic base such as pyridine or triethylamine in an inert solvent or the organic base as the solvent at a temperature of 0° to 150° C., preferably room temperature to 100° C.

Incidentally, $R^1$, $R^2$ and X in the formula [III] and [IV] are as defined above in the formula [I].

The compound represented by the formula [III], which is used as the starting material, is a 4-substituted methylimidazole. As specific examples, there can be mentioned 4-benzylimidazole, 4-(2,6-dimethylbenzyl)imidazole, 4-(2,5-dimethylbenzyl)imidazole, 4-(2,4,6-trimethylbenzyl)imidazole, 4-(2,3,4,6-tetramethylbenzyl)imidazole, 4-(2,3,5,6-tetramethylbenzyl)imidazole, 4-phenoxymethylimidazole and pyridinium methylimidazole.

As specific examples of the compound represented by the formula [IV], there can be mentioned N,N-dimethylcarbamoyl chloride, N-methyl-N-ethylcarbamoyl chloride, N,N-diethylcarbamoyl chloride, N-methyl-N-isopropylcarbamoyl chloride, N-methyl-N-cclohexylcarbamoyl chloride, N-methyl-N-(2propenyl)carbamoyl chloride, N-methyl-N-methoxycarbamoyl chloride, 1-piperidylcarbamoyl chloride, 3,5-dimethylpiperidylcarbonyl chloride, morpholinocarbonyl chloride, ethoxycarbonyl chloride, N,N-dimethylthiocarbamoyl chloride and 6-aza-bicyclo[3,2,1]octo-6-ylcarbonyl chloride.

2. Synthesis of Thioimidazole Derivative

The thioimidazole derivative represented by the above-mentioned formula [II] is synthesized according to the process represented by the following reaction formula:

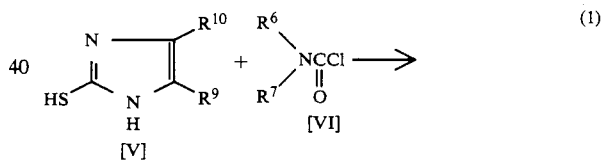

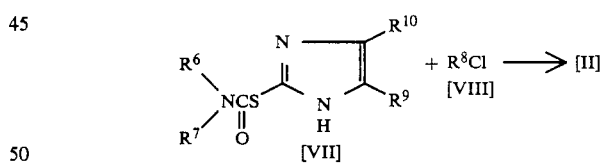

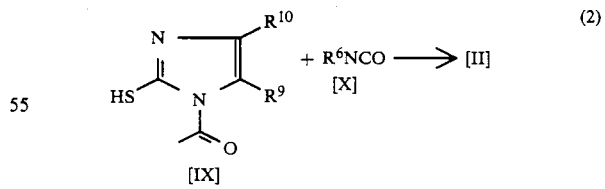

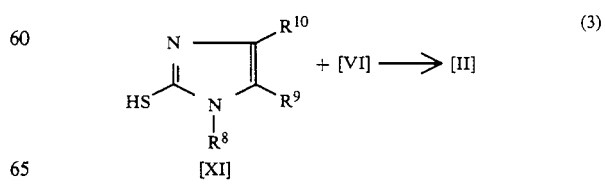

Incidentally, $R^6$ through $R^{10}$ in the formula [V] through [XI] are as defined above in the formula [II].

(1) In the case where $R^8$ of the compound [II] is an alkylcarbonyl group, an alkoxycarbonyl group or a dialkylaminocarbonyl group, the compound [II] is prepared by reacting compounds [V] and [VI] in the presence of an inorganic base such as potassium carbonate, sodium carbonate, sodium hydroxide or potassium t-butoxide or an organic base such as pyridine or triethylamine in an inert solvent or the abovementioned organic base as the solvent at a temperature of 0° to 200° C., preferably room temperature to 150° C., to form a compound [VII] and reacting this compound with a compound [VIII] under similar conditions.

(2) In the case where $R^7$ and $R^8$ of the compound [II] are one carbonyl group forming a ring, the compound [II] is prepared by reacting compounds [IX] and [X] in an inert solvent such as N,N-dimethylformamide in the presence of an organic base such as triethylamine at a temperature of 0° to 100° C., preferably room temperature to 50° C.

(3) In other case, the compound [II] is prepared by reacting compounds [XI] and [VI] in the presence of an inorganic base such as potassium carbonate, sodium carbonate, sodium hydroxide or potassium hydroxide or an organic base such as pyridine or triethylamine in an inert solvent or the above-mentioned organic base as the solvent at a temperature of 0° to 200° C., preferably room temperature to 150° C.

As specific examples of the compounds [V], [IX] and [XI] used as the starting materials, there can be mentioned 2-mercaptoimidazole, 2-mercapto-4-phenylimidazole, 1-acetyl-4-phenyl-2-mercaptoimidazole, 2-mercapto-4-(2-methylphenyl)imidazole, 2-mercapto-4-(4-methoxyphenyl)imidazole, 2-mercapto-4-(4-chlorophenyl)imidazole and 2-mercapto-4-(p-biphenyl)imidazole.

As specific examples of the compound of the formula [VI], there can be mentioned N,N-dimethylcarbamoyl chloride, N,N-diethylcarbamoyl chloride, N,N-di-n-propylcarbamoyl chloride, 1-piperidylcarbonyl chloride, morpholinocarbonyl chloride, thiomorpholinocarbonyl chloride and 1,2,3,4-tetrahydroquinolylcarbonyl chloride.

Specific examples of the imidazole derivative of the present invention will now be described.

First, specific examples of the N-substituted imidazole derivatives of the formula [I] are shown in Table 1.

TABLE 1

| Compound No. | $R^1$ | $CH_2-R^2$ | Compound Name |
|---|---|---|---|
| 1 |  |  | 4-benzyl-1-(N,N-dimethylcarbamoyl)-imidazole |
| 2 | " | 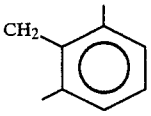 | 4-(2,6-dimethylbenzyl)-1-(N,N-dimethylcarbamoyl)imidazole |
| 3 | " | 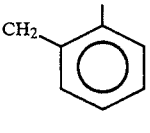 | 4-(2,5-dimethylbenzyl)-1-(N,N-dimethylcarbamoyl)imidazole |
| 4 | " | 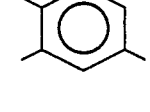 | 4-(2,4,6-trimethylbenzyl)-1-(N,N-dimethylcarbamoyl)imidazole |
| 5 | " | 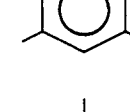 | 4-(2,3,4,6-tetramethylbenzyl)-1-(N,N-dimethylcarbamoyl)imidazole |
| 6 | " | 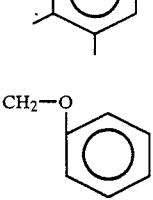 | 4-(2,3,5,6-tetramethylbenzyl)-1-(N,N-dimethylcarbamoyl)imidazole |
| 7 | " |  | 4-phenoxymethyl-1-(N,N-dimethylcarbamoyl)imidazole |

TABLE 1-continued

| Compound No. | R¹ | CH₂—R² | Compound Name |
|---|---|---|---|
| 8 |  N(Me)(Et) | 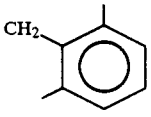 CH₂-(2,6-dimethylphenyl) | 4-(2,6-dimethylbenzyl)-1-(N,N-methylethylcarbamoyl)imidazole |
| 9 |  N(Me)(iPr) | " | 4-(2,6-dimethylbenzyl)-1-(N-methyl-N-isopropylcarbamoyl)imidazole |
| 10 | 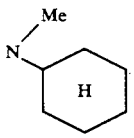 N(Me)(cyclohexyl) | " | 4-(2,6-dimethylbenzyl)-1-(N-methyl-N-cyclohexylcarbamoyl)imidazole |
| 11 |  N(Me)(allyl) | " | 4-(2,6-dimethylbenzyl)-1-N-methyl-N-(2-propenyl)-carbamoyl imidazole |
| 12 |  N(Me)(OMe) | " | 4-(2,6-dimethylbenzyl)-1-(N-methyl-N-methoxycarbamoyl)imidazole |
| 13 |  N(Et)(Et) | " | 4-(2,6-dimethylbenzyl)-1-(N,N-diethyl-carbamoyl)-imidazole |
| 14 | 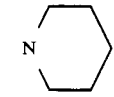 piperidinyl | 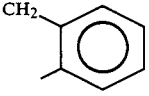 CH₂-aryl | 4-(2,6-dimethylbenzyl)-1-(1-piperodylcarbonyl)-imidazole |
| 15 | 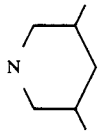 3,5-dimethylpiperidinyl | " | 4-(2,6-dimethylbenzyl)-1-(3,5-dimethyl-pyridylcarbonyl)imidazole |
| 16 |  1-azabicyclo[3,2,1]octyl | " | 4-(2,6-dimethylbenzyl)-1-(1-azabicycle[3,2,1]-octylcarbonyl)imidazole |
| 17 |  morpholino | " | 4-(2,6-dimethylbenzyl)-1-(morpholino-carbonyl)-imidazole |
| 18 | OEt | " | 4-(2,6-dimethylbenzyl)-1-(ethoxycarbonyl)-imidazole |
| 19 |  N(Me)(Me) | 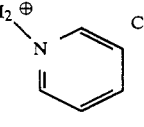 CH₂-pyridinium Cl⁻ | 4-[1-(N,N-dimethylcarbamoyl)]imidazoyl-methylpyridinium chloride |
| 20 |  N(Me)(Me) | " | 4-(2,6-dimethylbenzyl)-1-(N,N-dimethyl-thiocarbamoyl)imidazole |

Specific examples of the thioimidazole derivative represented by the formula [II] are shown in Table 2.

TABLE 2

| Compound No. | R⁶ | R⁷ | R⁸ | R⁹ | R¹⁰ | Compound Name |
|---|---|---|---|---|---|---|
| 21 | Me | Me | H | H |  | 2-(N,N-dimethylcarbamoyl-thio)-4-phenylimidazole |
| 22 | " | " | Me | " | " | 2-(N,N-dimethylcarbamoyl-thio)-1-methyl-4-phenyl-imidazole |
| 23 | " | " | Et | " | " | 2-(N,N-dimethylcarbamoyl-thio)-1-ethyl-4-phenyl-imidazole |
| 24 | " | " | n-Pr | " | " | 2-(N,N-dimethylcarbamoyl-thio)-1-propyl-4-phenyl-imidazole |
| 25 | " | " | i-Pr | " | " | 2-(N,N-dimethylcarbamoyl-thio)-1-isopropyl-4-phenyl-imidazole |
| 26 | " | " | 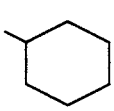 | " | " | 2-(N,N-dimethylcarbamoyl-thio)-1-cyclohexyl-4-phenyl-imidazole |
| 27 | " | " | 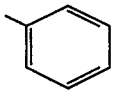 | " | " | 2-(N,N-dimethylcarbamoyl-thio)-1,4-diphenyl-imidazole |
| 28 | Me | Me | 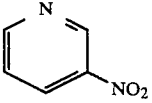 | H | 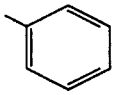 | 2-(N,N-dimethylcarbamoyl-thio)-1-(5-nitropyridinyl)-4-phenyl-imidazole |
| 29 | Me | Me | 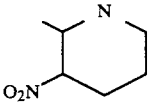 | H | " | 2-(N,N-dimethylcarbamoyl-thio)-1-(3-nitropyridinyl)-4-phenylimidazole |
| 30 | " | " | CONMe₂ | " | " | 1-(N,N-dimethylcarbamoyl)-2-(N,N-dimethylcarbamoyl-thio)-4-phenylimidazole |
| 31 | Me | Me | COOEt | H | " | 2-(N,N-dimethylcarbamoyl-thio)-1-ethoxycarbonyl-4-phenylimidazole |
| 32 | " | " | COCH₃ | " | " | 2-(N,N-dimethylcarbamoyl-thio)-1-acetyl-4-phenyl-imidazole |
| 33 | Me | i-Pr | COCH₃ | " | " | 2-(N-methyl-N-isopropyl-carbamonylthio)-1-acetyl-4-phenylimidazole |
| 34 | Et | Et | H | " | " | 2-(N,N-dimethylcarbamoyl-thio)-4-phenylimidazole |
| 35 | n-Pr | n-Pr | H | H | " | 2-(N,N-dipropylcarbamoyl-thio)-4-diphenylimidazole |
| 36 |  | | " | " | " | 2-pyrrolidinocarbonylthio-4-phenylimidazole |
| 37 |  | | H | H | " | 2-piperidinocarbonylthio-4-phenylimidazole |
| 38 | " | |  | " | " | 1-piperidinocarbonyl-2-piperidinocarbonylthio-4-phenylimidazole |

TABLE 2-continued

| Compound No. | R⁶ | R⁷ | R⁸ | R⁹ | R¹⁰ | Compound Name |
|---|---|---|---|---|---|---|
| 39 | morpholino (N–O ring) | | H | " | " | 2-morpholinocarbonylthio-4-phenylimidazole |
| 40 | thiomorpholino (N–S ring) | | " | " | " | 2-thiomorpholinocarbonyl-thio-4-phenylimidazole |
| 41 | 1,2,3,4-tetrahydroquinolyl | | " | " | " | 2-(1,2,3,4-tetrahydro-quinolyl)-carbonylthio-4-phenylimidazole |
| 42 | Me | Me | H | Me | " | 5-methyl-2-(N,N-dimethyl-carbamoylthio)-4-phenyl-imidazole |
| 43 | Me | Me | H | Et | " | 5-ethyl-2-(N,N-dimethyl-carbamoylthio)-4-diphenyl-imidazole |
| 44 | | " | COOEt | " | " | 2-(N,N-dimethylcarbamoyl-thio)-5-ethoxycarbonyl-4-phenylimidazole |
| 45 | Me | Me | H | H | 2-methylphenyl | 2-(N,N-dimethylcarbamoyl-thio)-4-(2-methylphenyl)-imidazole |
| 46 | | " | " | " | 4-methylphenyl | 2-(N,N-dimethylcarbamoyl-thio)-4-(4-methylphenyl)-imidazole |
| 47 | | " | " | " | 4-methoxyphenyl | 2-(N,N-dimethylcarbamoyl-thio)-4-(4-methoxyphenyl)-imidazole |
| 48 | | " | " | " | 4-chlorophenyl | 2-(N,N-dimethylcarbamoyl-thio)-4-(4-methoxyphenyl)-imidazole |
| 49 | | " | " | " | 4-phenylphenyl | 2-(N,N-dimethylcarbamoyl-thio)-4-(4-phenylphenyl)-imidazole |
| 50 | Me | Me | phenyl | H | H | 2-(N,N-dimethylcarbamoyl-thio)-1-phenylimidazole |
| 51 | | " | 2-methyl-5-nitropyridinyl | Et | H | 2-(N,N-dimethylcarbamoyl-thio)-1-(5-nitropyridinyl)-imidazole |

TABLE 2-continued

| Compound No. | R⁶ | R⁷ | R⁸ | R⁹ | R¹⁰ | Compound Name |
|---|---|---|---|---|---|---|
| 52 | | " | 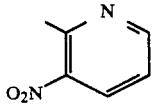 | H | H | 2-(N,N-dimethylcarbamoyl-thio)-1-(3-nitropyridinyl)-imidazole |
| 53 | Me | | C=O | H | 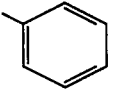 | 3-methyl-7-phenyl-1,3-5-thiadiazino[3,2-a]imidazole-2,4(3H)dione |
| 54 | Et | | C=O | " | " | 3-ethyl-7-phenyl 1,3,5-thiadiazino[3,2-a]imidazole-2,4(3H)dione |

The present invention will now be described in detail with reference to the following examples that by no means limit the scope of the invention.

EXAMPLE 1

Synthesis of 4-benzyl-1-(N,N-dimethylcarbamoyl)imidazole

In 3 ml of pyridine was dissolved 0.16 g (1.0 millimole) of 4-benzylimidazole, and 0.13 g (1.2 millimoles) of N,N-dimethylcarbamoyl chloride was added to the solution and the mixture was heated at 60° C. for 1 hour. Then, 10 ml of water and 20 ml of chloroform were added to the mixture to effect extraction.

The chloroform layer was concentrated and purified by the silica gel chromatography (developing solvent-=ethyl acetate) to obtain 0.66 g (yield=60%) of intended 4-benzyl-1-(N,N-dimethylcarbamoyl)imidazole (compound No. 1) in the form of a light brown oil.

¹H-Nuclear Magnetic Resonance Spectrum (chloroform-d, δppm): 3.08 (s, 6H), 3.95 (s, 2H), 6.88 (d, J=1.8 Hz, 1H), 7.31 (s, 6H), 7.87 (d, J=1.8 Hz, 1H)

By reacting compounds different from the abovementioned starting compounds in the kind of the substituents, compounds Nos. 2 through 20 were synthesized in the same manner as described above. The yields and physical properties are shown in Table 3.

TABLE 3

| Compound No. | ¹H-Nuclear Magnetic Resonance Spectrum (chloroform-d, δ ppm) | Melting Point (°C.) | Yield (%) |
|---|---|---|---|
| 2 | 2.34 (6H,s) 3.90 (2H,s) 6.52 (1H,d,J = 1.8 Hz) 7.06 (3H,s) 7.83 (1H,d,J = 1.8 Hz) | 107~109 | 45 |
| 3 | 2.25 (3H,s) 2.28 (3H,s) 3.05 (6H,s) 3.88 (2H,s) 6.72 (1H,d,J = 1.8 Hz) 7.00 (3H,m) 7.84 (1H,d,J = 1.8 Hz) | oil | 85 |
| 4 | 2.28 (9H,s) 3.04 (6H,s) 3.92 (2H,s) 6.52 (1H,d,J = 1.8 Hz) 6.87 (2H,s) 7.83 (1H,d,J = 1.8Hz) | oil | 100 |
| 5 | 2.20 (12H,m) 3.02 (6H,s) 3.96 (2H,s) 6.54 (1H,d,J = 1.8 Hz) 6.87 (1H,s) 7.83 (1H,d,J = 1.8 Hz) | oil | 70 |
| 6 | 2.20 (6H,s) 2.25 (6H,s) 3.04 (6H,s) 4.00 (2H,s) 6.54 (1H,d,J = 1.8 Hz) 6.91 (1H,s) 7.85 (1H,d,J = 1.8 Hz) | 107~110 | 70 |
| 7 | 3.13 (6H,s) 5.08 (2H,s) 6.8~7.4 (6H,m) 7.93 (1H,d,J = 1.8 Hz) | oil | 93 |
| 8 | 1.20 (3H,t,J = 7.2 Hz) 2.34 (6H,s) 3.00 (3H,s) 3.40 (2H,q,J = 7.2 Hz) 3.97 (2H,s) 6.52 (1H,d,J = 1.8 Hz) 7.06 (3H,s) 7.83 (1H,d,J = 1.8 Hz) | oil | 22 |
| 9 | 1.16 (3H,s) 1.24 (3H,s) 2.22 (6H,s) 2.84 (3H,s) 3.96 (2H,s) 4.28 (1H,m) 6.50 (1H,d,J = 1.8 Hz) 7.05 (3H,s) 7.80 (1H,d,J = 1.8 Hz) | oil | 50 |
| 10 | 1.0 2.0 (10H,m) 2.33 (6H,s) 2.85 (3H,s) 3.80 (1H,m) 3.98 (2H,s) 6.49 (1H,d,J = 1.8 Hz) 7.07 (3H,s) 7.84 (1H,d,J = 1.8 Hz) | oil | 66 |
| 11 | 2.32 (6H,s) 2.99 (3H,s) 3.90 (2H,m) 3.96 (2H,s) 5.22 (2H,m) 5.80 (1H,m) 6.56 (1H,d,J = 1.8 Hz) 7.05 (3H,s) 7.87 (1H,d,J = 1.8 Hz) | oil | 72 |
| 12 | 2.36 (6H,s) 3.36 (3H,s) 3.65 (3H,s) 3.98 (2H,s) 6.89 (1H,d,J = 1.8 Hz) 7.80 (3H,s) 8.22 (1H,d,J = 1.8 Hz) | 83~86 | 35 |
| 13 | 1.18 (6H,t,J = 7.2 Hz) 2.34 (6H,s) 3.36 (4H,q,J = 7.2 Hz) 3.98 (2H,s) 6.52 (1H,d,J = 1.8 Hz) 7.08 (3H,s) 7.82 (1H,d,J = 1.8 Hz) | oil | 33 |
| 14 | 1.62 (6H,m) 2.33 (6H,s) 3.20 (1H,m) 3.50 (4H,m) 3.97 (2H,s) 6.51 (1H,d,J = 1.8 Hz) 7.08 (3H,s) 7.80 (1H,d,J = 1.8 Hz) | 85~87 | 78 |
| 15 | 0.85 (6H,m) 1.4~2.0 (4H,m) 2.30 (6H,s) 2.9~3.6 (4H,m) 3.90 (2H,br,d,J = 16 Hz) 3.96 (2H,s) 6.46 (1H,d,J = 1.2 Hz) 7.01 (3H,s) 7.90 (1H,d,J = 1.2 Hz) | oil | 46 |
| 16 | 1.2 2.2 (8H,m) 2.34 (6H,s) 2.5 (1H,m) 3.3 3.8 (2H,m) 3.96 (2H,s) 4.25 (1H,m) 6.68 (1H,d,J = 1.8 Hz) 7.05 (3H,s) 7.97 (1H,d,J = 1.8 Hz) | oil | 58 |
| 17 | 2.33 (6H,s) 3.60 (8H,m) 3.96 (2H,s) 6.50 (1H,d,J = 1.8 Hz) 7.07 (3H,s) 7.81 (1H,d,J = 1.8 Hz) | 89 91 | 42 |
| 18 | 1.37 (3H,t,J = 7.2 Hz) 2.32 (6H,s) 3.96 (2H,s) | 52 54 | 72 |

TABLE 3-continued

| Compound No. | $^1$H-Nuclear Magnetic Resonance Spectrum (chloroform-d, δ ppm) | Melting Point (°C.) | Yield (%) |
|---|---|---|---|
|  | 4.40 (2H,q,J = 7.2 Hz) 6.70 (1H,d,J = 1.8 Hz) 7.07 (3H,s) 8.09 (1H,d,J = 1.8 Hz) | | |
| 19 | 3.13 (6H,s) 6.22 (2H,br,s) 7.92 (1H,s) 8.33 (1H,s) 6.98 7.13 (3H,m) 8.32 8.60 (2H,m) | deliquescent | 53 |
| 20 | 2.35 (6H,s) 3.29 (6H,s) 3.98 (2H,d,J = 3 Hz) 6.50 (1H,dt,J = 2.2 Hz) 7.50 (3H,s) 7.86 (1H,d,J = 2 Hz) | 138 140 | 73 |

EXAMPLE 2

Synthesis of 2-(N,N-dimethylcarbamoylthio)-4-phenyl-imidazole

In 50 ml of pyridine was dissolved 5.0 g (28.4 millimoles) of 2-mercapto-4-phenylimidazole, and 3.13 ml (34.1 millimoles) of N,N-dimethylcarbamoyl chloride was added to the solution and the mixture was heated at 70° C. for 3 hours. The reaction mixture was concentrated under reduced pressure, and 200 ml of water and 200 ml of chloroform were added to the concentrate to effect extraction. The chloroform layer was concentrated and the concentrate was recrystallized from ethanol to obtain 2.4 g (yield=34%) of intended 2-(N,N-dimethylcarbamoylthio)-4-phenylimidazole (compound No. 21) in the form of a colorless crystal.

Melting Point 183°–185° C.

$^1$H-Nuclear Magnetic Resonance Spectrum (chloroform-d, δppm): 3.08 (s, 6H), 7.30 (m, 3H), 7.70 (m, 3H)

By reacting compounds different from the abovementioned starting compounds in the kind of the substituent, compounds Nos. 22 through 27 and 34 through 50 were synthesized in the same manner as described above. The yields and physical properties are shown in Table 4.

TABLE 4

| Compound No. | $^1$H-Nuclear Magnetic Resonance Spectrum (chloroform-d, δ ppm) | Melting Point (°C.) | Yield (%) |
|---|---|---|---|
| 22 | 3.10 (6H,br,s) 3.76 (3H,s) 7.38 (5H,m) 7.80 (2H,m) | 119~121 | 17 |
| 23 | 1.47 (3H,t,J = 7.2 Hz) 3.10 (6H,br,s) 4.11 (2H,q,J = 7.2 Hz) 7.40 (3H,m) 7.80 (2H,m) | 108~110 | 11 |
| 24 | 0.96 (3H,t,J = 7.2 Hz) 1.82 (2H,m) 3.04 (6H,br,s) 4.0 (2H,t,J = 7.2 Hz) 7.35 (3H,m) 7.80 (2H,q,J | 102~103 | 21 |
| 25 | 1.44 (3H,s) 1.53 (3H,s) 3.10 (6H,br,s) 4.70 (1H,m) 7.2~7.7 (4H,m) 7.80 (2H,m) | 130~132 | 23 |
| 26 | 1.0~2.3 (10H,m) 3.10 (6H,m) 4.20 (1H,m) 7.40 (4H,m) 7.80 (2H,m) | 157~159 | 5 |
| 27 | 2.96 (6H,s) 7.2~7.6 (9H,m) 7.90 (2H,m) | 55~57 | 59 |
| 34 | 1.24 (6H,t,J = 7.2 (6H,s) 3.46 (4H,q,J = 7.2 Hz) 7.30 (4H,m) 7.70 (2H,m) | 176~178 | 45 |
| 35 | 0.95 (6H,t,J = 7.2 Hz) 1.70 (4H,m) 3.35 (4H,t,J = 7.2 Hz) 7.30 (4H,m) 7.70 (2H,m) | 107~109 | 62 |
| 36 | 2.0 (4H,m) 3.5 (4H,m) 7.30 (4H,m) 7.70 (2H,m) | 210~212 | 49 |
| 37 | 1.65 (6H,br,s) 3.55 (4H,br,s) 7.35 (4H,m) 7.75 (2H,m) | 189~191 | 31 |
| 38 | 1.62 (12H,br,s) 3.50 (8H,s) 7.40 (4H,m) 7.80 (2H,m) | 174~176 | 64 |
| 39 | 3.0 (4H,m) 3.8 (4H,m) 7.25 (4H,m) 7.70 (2H,m) | 185~189 | 55 |
| 40 | 2.70 (4H,m) 3.90 (4H,m) 7.25 (4H,m) 7.70 (2H,m) | 197~198 | 46 |
| 41 | 2.05 (2H,m) 2.80 (2H,m) 3.83 (2H,m) 7.25 (7H,m) 7.70 (2H,m) | 88~90 | 31 |
| 42 | 2.36 (3H,s) 3.10 (6H,s) 7.2~7.6 (5H,m) | 184~186 | 73 |
| 43 | 1.30 (3H,t,J = 7.2 Hz) 2.82 (2H,1,J = 7.2 Hz) 3.10 (6H,s), 7.2~7.6 (5H,m) 8.60 (1H,m) | 116~118 | 75 |
| 44 | 1.33 (3H,t,J = 7.0 Hz) 3.08 (6H,s) 4.33 (2H,q,J = 7.0 Hz) 7.20 7.60 (5H,m) | 148~151 | 84 |
| 45 | 2.32 (3H,s) 3.02 (6H,s) 7.00 (1H,s) 7.2~7.5 (4H,m) | amorphous | 85 |
| 46 | 2.35 (3H,s) 3.10 (H,s) 7.1~7.7 (5H,m) | 227~230 | 26 |
| 47 | 3.10 (6H,s) 3.83 (3H,s) 6.90 (2H,d,J = 8 Hz) 7.28 (1H,s) 7.52 (2H,d,J = 2 Hz) | 179~180 | 62 |
| 48 | 3.12 (6H,s) 7.20 (3H,m) 7.70 (2H,m) | 235~239 | 51 |
| 49 | 3.40 (6H,s) 7.16~8.00 (10H,m) | 217~220 | 61 |
| 50 | 2.96 (6H,s) 7.25~7.35 (2H,m) 7.44 (5H,s) | 112~113 | 13 |

EXAMPLE 3

Synthesis of 2-(N,N-dimethylcarbamoylthio)-1-(5-nitropyridinyl)-4-phenylimidazole To a solution of 0.25 g (1.0 millimole) of 2-(N,N-dimethylcarbamoylthio)-4-phenylimidazole in 10 ml of N, N-dimethylformamide was added 0.04 g (1.0 millimole) of sodium hydride, and the mixture was stirred at room temperature for 1 hour. Then, 0.16 g (1.0 millimole) of 2-chloro-5-nitropyridine was added to the mixture, and the mixture was stirred at room temperature for 3 hours. The mixture was concentrated under reduced pressure and washed with water and ethyl acetate to obtain 0.27 g (yield=73%) of intended 2-(N,N-dimethylcarbamoylthio)-1-(5-nitropyridinyl)-4-phenylimidazole (compound No. 28) in the form of a yellow powder.

Melting Point 200°–201° C.

$^1$H-Nuclear Magnetic Resonance Spectrum (dimethylsulfoxide-d, δppm): 2.60 (br, s, 6H), 7.40–7.70 (4H, m), 7.80–8.0 (2H, m), 8.16 (1H, m), 8.52 (1H, d, J=8 Hz), 9.20 (1H, m)

By reacting compounds different from the abovementioned starting compounds in the kind of the substituent, compounds Nos. 29, 51 and 52 were similarly prepared. The yields and physical properties are shown in Table 5.

TABLE 5

| Compound No. | $^1$H-Nuclear Magnetic Resonance Spectrum (chloroform-d, δ ppm) | Melting Point (°C.) | Yield (%) |
|---|---|---|---|
| 29 | 2.90 (6H,br,s) 7.20 7.80 (5H,m) 7.86 (2H,m) 8.50 (1H,d,J = 8 Hz) 8.84 (1H,d,J = 5 Hz) | 163~165 | 40 |
| 51 | 3.05 (6H,br,s) | 174~175 | 52 |

TABLE 5-continued

| Compound No. | $^1$H-Nuclear Magnetic Resonance Spectrum (chloroform-d, δ ppm) | Melting Point (°C.) | Yield (%) |
|---|---|---|---|
| | 7.40 (1H,d,J = 1.2 Hz)<br>7.84 (1H,d,J = 1.2 Hz)<br>8.00 (1H,dd,J = 6,9 Hz)<br>8.65 (1H,dd,J = 1.2,9 Hz)<br>9.00 (1H,dd,J = 1.2,6 Hz) | | |
| 52 | 3.04 (6H,br,s) 7.40 (1H,d,J = 1.2 Hz)<br>7.84 (1H,d,J = 1.2 Hz)<br>8.03 (1H,d,J = 9.0 Hz)<br>8.65 (1H,dd,J = 1.2,9.0 Hz)<br>9.40 (1H,d,J = 1.2 Hz) | 102~110 | 44 |

EXAMPLE 4

Synthesis of 1-(N,N-dimethylcarbamoyl)-2-(N,N-dimethylcarbamoylthio)-4-phenylimidazole In 5 ml of pyridine was dissolved 0.70 g (2.84 millimoles) of 2-(N,N-dimethylcarbamoylthio)-4-phenylimidazole, and 0.26 ml (2.84 millimoles) of N,N-dimethylcarbamoyl chloride was added to the solution and the mixture was heated at 120° C. for 5 hours. The mixture was concentrated under reduced pressure and 20 ml of water and 20 ml of chloroform were added to the concentrate to effect extraction. The chloroform layer was dried and concentrated under reduced pressure to obtain 0.9 g (yield=100%) of intended 1-(N,N-dimethylcarbamoyl)-2-(N,N-dimethylcarbamoylthio)-4-phenylimidazole (compound No. 30) in the form of a light brown oil.

$^1$H-Nuclear Magnetic Resonance Spectrum (chloroform-d, δppm): 3.02 (6H, s), 3.08 (6H, s), 7.1-7.6 (4H, m), 7.80 (2H, m)

By reacting compounds different from the abovementioned starting compounds in the kind of the substituent, compounds Nos. 31, 32 and 33 were similarly synthesized. The yield and physical properties are shown in Table 6.

TABLE 6

| Compound No. | $^1$H-Nuclear Magnetic Resonance Spectrum (chloroform-d, δ ppm) | Melting Point (°C.) | Yield (%) |
|---|---|---|---|
| 31 | 1.43 (3H,t,J = 7.2 Hz) 3.06 (6H,s)<br>4.50 (2H,q,J = 7.2 Hz) 7.40 (3H,m)<br>7.84 (3H,m) | 129~131 | 99 |
| 32 | 2.68 (3H,s) 2.96 (6H,br,s)<br>7.40 (3H,m) 7.85 (2H,m)<br>8.48 (1H,s) | 172~174 | 85 |
| 33 | 1.16 (6H,br,d,J = 7.2 Hz)<br>2.69 (3H,s) 2.84 (3H,br,s)<br>4.10 (1H,m) 7.27 (3H,m)<br>7.86 (2H,m) 8.50 (1H,s) | 146~148 | 59 |

EXAMPLE 5

Synthesis of 3-methyl-7-phenyl-1,3,5-thiadiazino[3,2-a]imidazole-2,4(3H)-dione

In 10 ml of N,N-dimethylformamide was dissolved 0.6 g (2.75 millimoles) of 1-acetyl-4-phenyl-2-mercaptoimidazole, and 1.0 ml of triethylamine was added to the solution. Then, 0.65 ml (10.9 millimoles) of methyl isocyanate was further added to the solution and the mixture was stirred at room temperature overnight. Then, 20 ml of water was added to the reaction mixture, and the mixture was stirred for 1 hour and the precipitated crystal was recovered by filtration to obtain 0.4 g (yield=56%) of intended 3-methyl-7-phenyl-1,3,5-thiadiazino[3,2-a]imidazole-2,4(3H)-dione (compound No.53).

Melting Point 228°-229° C.

$^1$H-Nuclear Magnetic Resonance Spectrum (chloroform-d, δppm): 3.40 (3H, s), 7.50 (3H, m), 8.0 (2H, m), 8.58 (1H, s)

By reacting compounds different from the abovementioned starting compounds in the kind of the substituent, compound No. 54 was similarly obtained in the form of a colorless crystal (the yield was 16%).

Melting Point 213°-215° C.

$^1$H-Nuclear Magnetic Resonance Spectrum (chloroform-d, δppm): 1.35 (3H, t, J=7.2 Hz), 4.20 (2H, q, J=7.2 Hz), 7.40 (3H, m), 7.80 (2H, m), 8.04 (1H, s)

With respect to each of the above-mentioned compounds (compounds Nos. 1 through 54), the anti-hypoxia action was tested according to the following method and was evaluated by the life prolongation ratio. The obtained results are shown in Table 7.

Method of Evaluation of Anti-Hypoxia Action

Male mice of the ddy-line, which were 5 to 8 weeks old, were used as test animals, and they were divided into groups, each consisting of 7 to 10 mice. The compound to be tested was dissolved in a physiological saline solution. If the compound to be tested was insoluble, the compound was suspended in 1% gum arabic. The solution or suspension was administered in the abdominal cavity at a dose of 25 mg/kg and when 30 minutes had passed from the point of the administration, the mice were independently placed one by one into a desiccator (capacity=1 liter) and the pressure in the desiccator was reduced to 180 mmHg by a vacuum pump.

The period of from the point of initiation of the reduction of the pressure to the point of the stop of breathing was regarded as the existence time. When the mouse lived for more than 15 minutes, the calculation was done while regarding the existence time as being 15 minutes.

The significant difference test of the existence time was carried out according to the student t-test method using controls to which a physiological saline solution alone had been administered. The ratio of the existence time of the sample-administered group to the existence time of the physiological saline solution-administered control group was calculated as the life prolongation ratio.

TABLE 7

| Compound No. | Life Prolongation Ratio |
|---|---|
| 1 | 0.85 |
| 2 | 3.05 |
| 3 | — |
| 4 | 1.84 |
| 5 | — |
| 6 | — |
| 7 | — |
| 8 | — |
| 9 | 4.66 |
| 10 | 2.53 |
| 11 | 2.55 |
| 12 | 1.09 |
| 13 | 2.81 |
| 14 | 2.70 |
| 15 | — |
| 16 | 2.38 |
| 17 | 1.65 |

TABLE 7-continued

| Compound No. | Life Prolongation Ratio |
| --- | --- |
| 18 | 1.82 |
| 19 | 1.09 |
| 20 | 2.43 |
| 21 | 2.83 |
| 22 | 2.30 |
| 23 | 2.64 |
| 24 | 1.63 |
| 25 | 1.19 |
| 26 | 1.32 |
| 27 | 1.46 |
| 28 | 1.02 |
| 29 | 1.10 |
| 30 | 1.15 |
| 31 | 1.23 |
| 32 | 2.81 |
| 33 | 1.27 |
| 34 | 1.00* |
| 35 | 0.87* |
| 36 | 0.94* |
| 37 | 0.85* |
| 38 | 1.13 |
| 39 | 1.04* |
| 40 | 0.93* |
| 41 | 0.76* |
| 42 | 1.92 |
| 43 | 1.21 |
| 44 | 1.43 |
| 45 | 1.92 |
| 46 | 0.95* |
| 47 | 1.65 |
| 48 | 1.15* |
| 49 | 1.27 |
| 50 | 1.27 |
| 51 | 2.45** |
| 52 | 1.92** |
| 53 | 1.45 |
| 54 | 1.37 |

Note
*administration dose = 12.5 mg/kg
**administration dose = 50 mg/kg

The relation between the life prolongation ratio and the improvement of the brain function will now be described.

The brain is a texture weakest against hypoxia. When the oxygen concentration is reduced by reducing the pressure (hypobaric hypoxia; the state where a man climbs a high mountain), the functions of brain cells (electrical excitation, synthesis of transmitting substances, secretive action, etc.) are reduced. Accordingly, also the functions of the brain stem (where the respiratory center, the vasomotor center and the like are present) important for maintenance of life are lowered, and animals are caused to die. Therefore, a medicine having s brain function-improving action improves the life prolongation ratio.

Incidentally, the anti-hypoxia action means an effect of a medicine for prolonging the time to death by a hypoxia load.

We claim:

1. An N-substituted imidazole derivative represented by the following structural formula (I) or a pharmaceutically acceptable acid addition salt thereof:

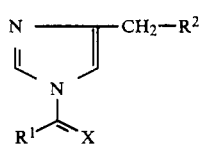
(I)

wherein $R^1$ stands for $NR^3R^4$ or $OR^5$, (in which $R^3$ and $R^4$ independently stand for a lower alkyl group, a lower alkenyl group, a cycloalkyl group or a lower alkoxy group, or $R^3$ and $R^4$ form a 5- to 8-membered saturated ring together with the nitrogen atom to which $R^3$ and $R^4$ are bonded, with the proviso that said ring may contain a nitrogen atom, a sulfur atom or an oxygen atom therein, and said ring may contain a lower alkyl group or a lower alkoxyl group as a ring substituent and two alkyl substitutents on said ring may further form a ring and $R^5$ stands for a lower alkyl group), $R^2$ stands for a phenyl group, a phenoxy group or a pyridyl group attached to the methylene group ($CH_2$—) via the ring nitrogen atom, and which phenyl group, phenoxy group or pyridyl group may be substituted by a lower alkyl group, a lower alkoxyl group, a halogen atom or an amino group, and X stands for an oxygen atom or a sulfur atom.

2. An N-substituted imidazole derivative or a pharmacologically acceptable acid addition salt thereof according to claim 1, wherein the N-substituted imidazole is represented by the following structural formula:

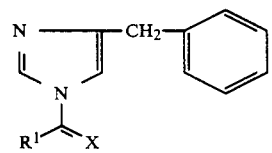

wherein $R^1$ and X are as defined in the formula [I].

3. An N-substituted imidazole derivative or a pharmacologically acceptable acid addition salt thereof according to claim 1, wherein the N-substituted imidazole derivative is represented by the following structural formula:

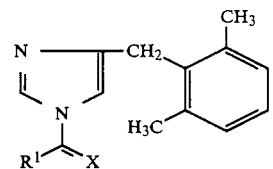

wherein $R^1$ and X are as defined in the formula [I].

4. An N-substituted imidazole derivative or a pharmacologically acceptable acid addition salt thereof according to claim 1, wherein the N-substituted imidazole derivative is represented by the following structural formula:

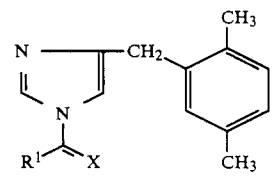

wherein $R^1$ and X are as defined in the formula [I].

5. An N-substituted imidazole derivative or a pharmacologically acceptable acid addition salt thereof according to claim 1, wherein the N-substituted imidazole derivative is represented by the following structural formula:

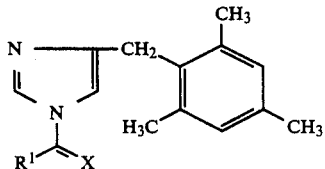

wherein R¹ and X are as defined in the formula [I].

6. An N-substituted imidazole derivative or a pharmacologically acceptable acid addition salt thereof according to claim 1, wherein the N-substituted imidazole derivative is represented by the following structural formula:

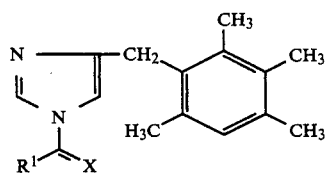

wherein R¹ and X are as defined in the formula [I].

7. An N-substituted imidazole derivative or a pharmacologically acceptable acid addition salt thereof according to claim 1, wherein the N-substituted imidazole derivative is represented by the following structural formula:

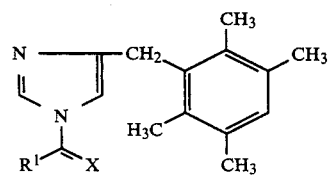

wherein R¹ and X are as defined in the formula [I].

8. An N-substituted imidazole derivative or a pharmacologically acceptable acid addition salt thereof according to claim 1, wherein the N-substituted imidazole derivative is represented by the following structural formula:

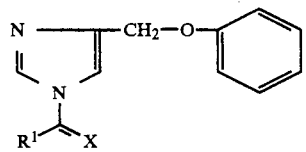

wherein R¹ and X are as defined in the formula [I].

9. An N-substituted imidazole derivative or a pharmacologically acceptable acid addition salt thereof according to claim 1, wherein the N-substituted imidazole derivative is represented by the following structural formula:

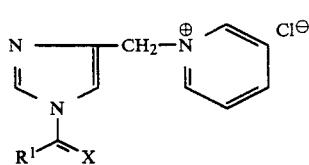

wherein R¹ and X are as defined in the formula [I].

10. An N-substituted imidazole derivative or a pharmacologically acceptable acid addition salt thereof according to claim 1, wherein the N-substituted imidazole derivative is represented by the following structural formula:

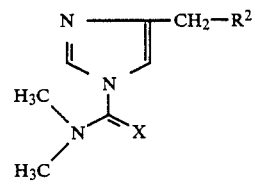

wherein R² and X are as defined in the formula [I].

11. An N-substituted imidazole derivative or a pharmacologically acceptable acid addition salt thereof according to claim 1, wherein the N-substituted imidazole derivative is represented by the following structural formula:

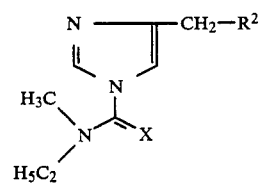

wherein R² and X are as defined in the formula [I].

12. An N-substituted imidazole derivative or a pharmacologically acceptable acid addition salt thereof according to claim 1, wherein the N-substituted imidazole derivative is represented by the following structural formula:

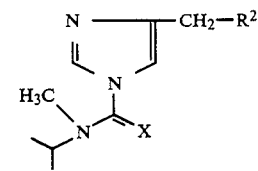

wherein R² and X are as defined in the formula [I].

13. An N-substituted imidazole derivative or a pharmacologically acceptable acid addition salt thereof according to claim 1, wherein the N-substituted imidazole derivative is represented by the following structural formula:

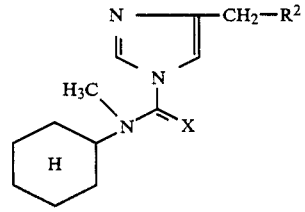

wherein R² and X are as defined in the formula [I].

14. An N-substituted imidazole derivative or a pharmacologically acceptable acid addition salt thereof according to claim 1, wherein the N-substituted imidazole derivative is represented by the following structural formula:

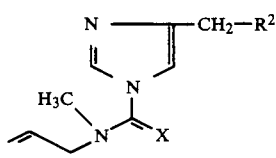

wherein $R^2$ and X are as defined in the formula [I].

15. An N-substituted imidazole derivative or a pharmacologically acceptable acid addition salt thereof according to claim 1, wherein the N-substituted imidazole derivative is represented by the following general formula:

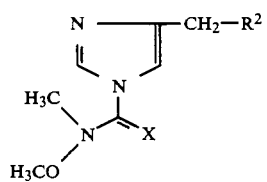

wherein $R^2$ and X are as defined in the formula [I].

16. An N-substituted imidazole derivative or a pharmacologically acceptable acid addition salt thereof according to claim 1, wherein the N-substituted imidazole derivative is represented by the following structural formula:

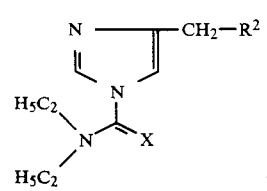

wherein $R^2$ and X are as defined in the formula [I].

17. An N-substituted imidazole derivative or a pharmacologically acceptable acid addition salt thereof according to claim 1, wherein the N-substituted imidazole derivative is represented by the following structural formula:

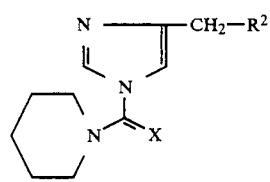

wherein $R^2$ and X are as defined in the formula [I].

18. An N-substituted imidazole derivative or a pharmacologically acceptable acid addition salt thereof according to claim 1, wherein the N-substituted imidazole derivative is represented by the following structural formula:

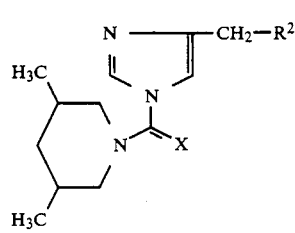

wherein $R^2$ and X are as defined in the formula [I].

19. An N-substituted imidazole derivative or a pharmacologically acceptable acid addition salt thereof according to claim 1, wherein the N-substituted imidazole derivative is represented by the following structural formula:

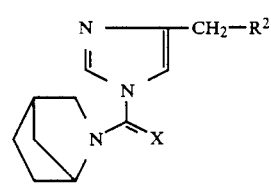

wherein $R^2$ and X are as defined in the formula [I].

20. An N-substituted imidazole derivative or a pharmacologically acceptable acid addition salt thereof according to claim 1, wherein the N-substituted imidazole derivative is represented by the following structural formula:

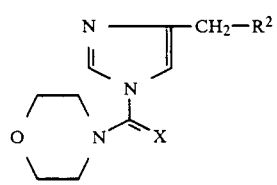

wherein $R^2$ and X are as defined in the formula [I].

21. An N-substituted imidazole derivative or a pharmacologically acceptable acid addition salt thereof according to claim 1, wherein the N-substituted imidazole derivative is represented by the following structural formula:

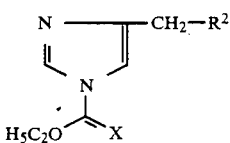

wherein $R^2$ and X are as defined in the formula [I].

22. A pharmaceutical composition having antihypoxia action comprising, as an active ingredient, an effective amount of an N-substituted imidazole derivative represented by the following structural formula

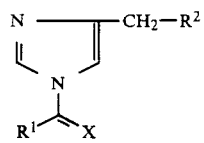

(I)

wherein $R^1$ stands for $NR^3R^4$ or $OR^5$, (in which $R^3$ and $R^4$ independently stand for a lower alkyl group, a lower alkenyl group, a cycloalkyl group or a lower alkoxy group, or $R^3$ and $R^4$ form a 5- to 8-membered saturated ring together with the nitrogen atom to which $R^3$ and $R^4$ are bonded, with the proviso that said ring may contain a nitrogen atom, a sulfur atom or an oxygen atom therein, and said ring may contain a lower alkyl group or a lower alkoxyl group as a ring substituent and two alkyl substituents on said ring may further form a ring and $R^5$ stands for a lower alkyl group), $R^2$ stands for a phenyl group, a phenoxy group or a pyridyl group attached to the methylene group ($CH_2-$) via the ring nitrogen atom, and which phenyl group, phenoxy group or pyridyl group may be substituted by a lower alkyl group, a lower alkoxy group, a halogen atom or an amino group, and X stands for an oxygen atom or a sulfur atom or a pharmaceutically acceptable acid addition salt thereof, in combination with a pharmacologically acceptable carrier.

* * * * *